(12) United States Patent
Mühlegger et al.

(10) Patent No.: US 6,403,786 B1
(45) Date of Patent: Jun. 11, 2002

(54) HETEROCYCLIC COMPOUNDS AND THEIR USE FOR ISOLATING NUCLEIC ACIDS

(75) Inventors: Klaus Mühlegger, Polling; Herbert Von der Eltz, Weilheim, both of (DE)

(73) Assignee: Roche Molecular Systems, Inc., Alameda, CA (US)

( * ) Notice: Subject to any disclaimer, the term of this patent is extended or adjusted under 35 U.S.C. 154(b) by 0 days.

(21) Appl. No.: 09/254,644

(22) PCT Filed: Sep. 11, 1997

(86) PCT No.: PCT/EP97/04972

§ 371 (c)(1),
(2), (4) Date: Jul. 2, 1999

(87) PCT Pub. No.: WO98/11104

PCT Pub. Date: Mar. 19, 1998

(30) Foreign Application Priority Data

Sep. 12, 1996 (DE) .......................... 196 37 042

(51) Int. Cl.[7] .................. C07H 19/10; C07H 19/01; A61K 31/70
(52) U.S. Cl. ................. 536/26.8; 536/26.1; 536/23.1; 536/24.3; 514/49; 514/51
(58) Field of Search .................. 536/26.8, 26.1, 536/23.1, 24.3; 514/49, 51

(56) References Cited

U.S. PATENT DOCUMENTS 5,328,824 A * 7/1994 Ward et al.

FOREIGN PATENT DOCUMENTS

| WO | 0285058 | * 10/1988 |
| WO | 9316094 | * 8/1993 |

* cited by examiner

Primary Examiner—Ralph Gitomer
Assistant Examiner—Devesh Khare
(74) Attorney, Agent, or Firm—Pennie & Edmonds LLP

(57) ABSTRACT

The invention concerns compounds of the general formula (I) in which the residues $R_1$ to $R_7$ have the meanings given in the application as well as methods for their preparation. The compounds are in particular suitable as substrates for RNA or DNA polymerases and can thus be incorporated into RNA or DNA oligonucleotides and are especially suitable for labelling and detecting nucleic acids or for DNA sequencing.

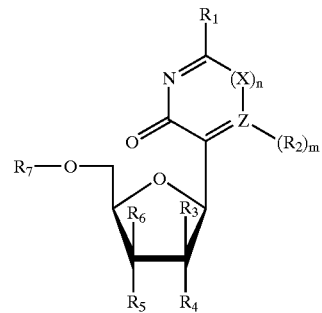

19 Claims, 1 Drawing Sheet

HETEROCYCLIC COMPOUNDS AND THEIR USE FOR ISOLATING NUCLEIC ACIDS

The invention concerns heterocyclic compounds which can be used to label, detect and sequence nucleic acids.

Nucleic acids are of major importance in the living world as carriers and transmitters of genetic information. Since their discovery by F. Miescher they have aroused a wide scientific interest which has led to the elucidation of their function, structure and mechanism of action.

An important tool for explaining these connections and for solving the problems was and is the detection of nucleic acids and namely with regard to their specific detection as well as with regard to their sequence i.e. their primary structure.

The specific detectability of nucleic acids is based on the property of these molecules to interact, i.e. to hybridize, with other nucleic acids to form base pairs by means of hydrogen bridges. Nucleic acids (probes) labelled in a suitable manner, i.e. provided with indicator groups, can thus be used to detect complementary nucleic acids (target).

The determination of the primary structure (sequence), i.e. the sequence of the heterocyclic bases of a nucleic acid, is achieved by means of sequencing techniques. Knowledge of the sequence is in turn a basic requirement for a targeted and specific use of nucleic acids for molecular biological problems and working techniques.

The sequencing also ultimately utilizes the principle of specific hybridization of nucleic acids to one another. As mentioned above labelled nucleic acid fragments are also used for this. Hence a suitable labelling of nucleic acids is an essential prerequisite for any detection method.

At an early period radioactive labelling was mainly used with suitable isotopes such as $^{32}P$ or $^{35}S$. However, the disadvantages of using radioactive reagents are obvious: such work requires special room facilities and licences as well as a controlled and elaborate disposal of the radioactive waste. The reagents for radioactive labelling are expensive. It is not possible to store such labelled probes for long periods due to the short half-life of the above-mentioned nuclides.

Therefore many attempts have been made in recent years to circumvent these serious disadvantages i.e. to get away from using a radioactive label. However, the high sensitivity of this type of label should be retained as far as possible.

Major advances have in fact already been achieved [see e.g. Nonradioactive Labeling and Detection of Biomolecules (Kessler, C., publ.) Springer Verlag Berlin, Heidelberg 1992].

An essential requirement for any detection of a nucleic acid is the prior labelling. As indicated above it is desirable to achieve this in a non-radioactive manner. Whereas radioactive labelling of nucleic acids is usually carried out by the enzymatically catalysed incorporation of appropriate radioactive nucleoside triphosphates, non-radioactive labelling has to be achieved by incorporating a suitable signal or reporter group.

Haptens (such as biotin or digoxigenin), enzymes (such as alkaline phosphatase or peroxidase) or fluorescent dyes (such as fluorescein or rhodamine) have, among others, mainly proven to be suitable as non-radioactive indicator molecules. These signal groups can be attached to or incorporated in nucleic acids by various methods.

A relatively simple procedure is for example to label the 5' end of an oligonucleotide provided with a terminal amino group by means of activated indicator molecules of the above-mentioned type. However, this only allows the introduction of one or a few indicator molecules into only a low molecular oligomer whereas a denser labelling of longer chain, high molecular nucleic acids with the aim of achieving a high sensitivity usually has to be accomplished by incorporating nucleoside triphosphates provided with reporter groups by means of polymerases as in a de novo synthesis.

Such current methods are known to a person skilled in the art as nick translation [Rigby, P. W. et al., (1977), J.Mol.Biol. 113, 237] and random primed labeling [Feinberg, A. P. & Vogelstein, B. (1984) Anal.Biochem. 137, 266]. A further method is the so-called 3'-tailing reaction with the aid of the enzyme terminal transferase [e.g. Schmitz, G. et al (1991) Anal.Biochem. 192, 222].

The nucleoside triphosphates which have been previously used in these methods are almost exclusively appropriately modified derivatives of the heterocyclic bases adenine, guanine, cytosine and thymine in the deoxyribonucleotide series or adenine, guanine, cytosine and uracil in the ribonucleotide series. Such derivatives are described for example by Langer et al. in Proc.Natl.Acad.Sci. USA 78, 6635 (1981), Mühlegger et al. Biol.Chem. Hoppe-Seyler 371, 953 (1990) and in EP 0 063 879. In this case the building blocks which occur naturally in DNA and RNA are used in a labelled form i.e. provided with signal groups.

The main disadvantages of these N-nucleosides is that the N-glycosidic bond is sensitive to acidic pH conditions and they can be degraded by nucleases.

Furthermore individual C-nucleosides (see e.g. Suhadolnik, R. J. in "Nucleoside Antibiotics", Wiley-Interscience, New York 1970) and their use in the therapeutic (antiviral or cancerostatic) field has also been known for a long time. In addition fluorescent C-nucleoside derivatives and their incorporation into DNA and RNA oligonucleotides has been described (WO 93/16094). The so-called intrinsic fluorescence of these nucleosides is, however, many times lower with regard to quantum yield than that of the special fluorophores such as fluorescein or corresponding rhodamine derivatives. A further disadvantage of the self-fluorescent C-nucleosides is their comparatively low excitation and emission wavelengths. As a result detection systems which are based on such derivatives only have a low sensitivity of detection and on the other hand influences of the measuring environment which interfere spectrally (such as biological material, autofluorescence of gel matrices etc.) have a very major effect. Hence the known nucleosides and nucleoside derivatives have a series of disadvantages which especially have an adverse effect on the detection of nucleic acids. Hence the object of the invention is to provide nucleoside derivatives modified with signal groups for the detection of nucleic acids which do not have the aforementioned disadvantages i.e. in particular are more stable and at the same time capable of being processed enzymatically and are suitable for the detection of nucleic acids at a practicable wavelength.

The object is achieved by heterocyclic compounds of the general formula I

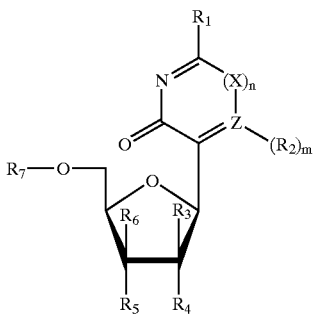

in which

R₁ and R₂ can be the same or different and represent hydrogen, oxygen, halogen, hydroxy, thio or substituted thio, amino or substituted amino, carboxy, lower alkyl, lower alkenyl, lower alkinyl, aryl, lower alkyloxy, aryloxy, aralkyl, aralkyloxy or a reporter group, R₃ and R₄ each represent hydrogen, hydroxy, thio or substituted thio, amino or substituted amino, lower alkyloxy, lower alkenoxy, lower alkinoxy, a protecting group or a reporter group, R₅ represents hydrogen, hydroxy, thio or substituted thio, amino or a substituted amino group, a reactive trivalent or pentavalent phosphorus group such as e.g. a phosphoramidite or H-phosphonate group, an ester or amide residue that can be cleaved in a suitable manner or a reporter group, R₄ and R₅ together form a further bond between C-2' and C-3' or an acetal group, R₆ represents hydrogen or a hydroxy, thio or substituted thio, amino or substituted amino group, R₇ represents hydrogen, a monophosphate, diphosphate or triphosphate group or the alpha, beta or gamma thiophosphate analogue of this phosphoric acid ester or a protective group as well as possible tautomers and salts thereof.

X denotes methylene or methine substituted with halogen, hydroxy, thio or substituted thio, amino or substituted amino, carboxy, lower alkyl, lower alkenyl, lower alkinyl, aryl, lower alkyloxy, aryloxy, aralkyl, aralkyloxy or a reporter group, or oxygen and n=0 or 1, Z denotes nitrogen or carbon provided that if Z denotes nitrogen, m is zero (0) and if X represents methylene, substituted methylene or substituted methine, Z cannot be carbon and if X denotes oxygen, Z cannot be nitrogen.

All detectable groups come into consideration as a reporter group such as in particular haptens, a fluorophore, a metal-chelating group, a lumiphore, a protein or an intercalator.

Those compounds of the general formula I are preferred in which the acetal group of the residues R₄ and R₅ is substituted with a reporter group. The reporter group can be bound directly or indirectly i.e. via a linker group.

In addition those compounds of the general formula I have proven to be particularly suitable in which R₁ can represent oxygen, R₂ can represent hydrogen or a reporter group, R₃ and R₄ can represent hydrogen, R₅ can represent hydroxy, hydrogen, a reactive trivalent or pentavalent phosphorus group, R₆ can represent hydrogen and R₇ can represent hydrogen, monophosphate, diphosphate or triphosphate groups.

Compounds of the general formula I are also preferred in which the reporter group is bound to the heterocyclic or tetrahydrofuran ring by means of a so-called linker group. Suitable linker groups are known to a person skilled in the art (see e.g. Mühlegger, K. et al. (1990) Biol.Chem. Hoppe-Seyler 371, 953–965 or Livak, K. J. et al. (1992) Nucl.Acids Res. 20, 4831–4837).

Compounds of the general formula I are additionally preferred in which R₁ represents hydrogen, hydroxy, an amino group, an optionally substituted amino group or a reporter group, R₂ represents an optionally substituted amino group or a reporter group, R₃ represents hydrogen, R₄ represents hydrogen, hydroxy, amino or substituted amino, lower alkyloxy, lower alkenoxy, lower alkinoxy, R₅ represents hydrogen, hydroxy, thio, an optionally substituted amino group, a phosphoramidite or a reporter group, R₄ and R₅ together represent an acetal group, R₆ represents hydrogen and R₇ represents a triphosphate group.

Compounds of formula I are also preferred in which X denotes oxygen and at the same time Z represents carbon substituted with R₂ or Z denotes nitrogen and at the same time X represents methylene or methine substituted with amino or substituted amino, carboxy or with a reporter group.

A further preferred embodiment is compounds according to formula I in which X=0 and Z represents methine substituted with amino or substituted amino, carboxy or with a reporter group.

The compounds according to the invention can be synthesized in various ways. In some cases one can start with naturally occurring precursors such as for example 3-(3,4-dihydroxy-5-hydroxymethyl-tetrahydrofuran-2-yl)-pyrrol-2,5-dione or 3-(3,4-dihydroxy-5-hydroxy-methyl-tetrahydrofuran-2-yl)-oxazine-2,6-dione. The important 3-(3-deoxy-4-hydroxy-5-hydroxymethyl-tetrahydrofuran-2-yl) derivatives are synthesized from these precursors by deoxygenation preferably according to Barton (Barton, D. H. R & Motherwell, W. B. (1981) Pure Appl.Chem. 53, 15).

In addition the chemical synthesis of the new heterocyclic compounds can for example be carried out as for example described in detail by K. A. Watanabe in "Chemistry of Nucleosides and Nucleotides" 3, 421–535 (L.B. Townsend, publ.) Plenum Press, New York and London, 1994.

Other syntheses of the said starting compounds have for example bean described by Hosmane, R. S. et al. in Bioorg. & Med.Chem.Lett. 3, 2847 (1993) and by Townsend, L. B. et al. in Tetrahedron Lett. 36, 8363 (1995).

The use of the compounds according to the invention to label nucleic acids with diverse, defined signal groups and hence to detect and sequence nucleic acids has proven to be particularly advantageous.

The substances according to the invention of the general formula I have a number of advantages especially compared to the classical nucleosides and nucleotides such as adenosine, guanosine, cytidine, thymidine, uridine etc. and their corresponding phosphoric acid esters.

One advantage is chemical stability i.e. towards acidic pH conditions. A further major advantage is the stability of these compounds towards enzymatic degradation by endonucleases and exonucleases. These enzymes are present in biological material and can severely interfere with the nucleic acid detection. On the other hand it is known that DNA and RNA polymerases are critical with regard to the acceptance of more or less modified nucleoside 5'-triphosphates i.e. with regard to the recognition and incorporation of such nucleotides as substrates in de novo synthesis. Experience has shown that the attachment of signal groups to nucleotides influences in particular their incorporation and incorporation rate.

The fact that the derivatives according to the invention can be incorporated by suitable polymerase into nucleic acids in a very efficient manner such as e.g. by the aforementioned methods of nick translation or of random primed labelling cannot be inferred from the prior art and must therefore be regarded as surprising for a person skilled in the art.

The said methods are used quite generally in nucleic acid detection e.g. for quantitative detection using blotting techniques on membranes or also in microtitre plates.

In sequencing, i.e. detecting the sequence of a nucleic acid, a complementary opposite strand is newly synthesized on the nucleic acid to be sequenced with the aid of a short (start)oligonucleotide (primer) and the addition of labelled nucleoside triphosphates and a polymerase, subsequently so-called termination reactions are carried out and the nucleic acid fragments that are generated in this process are separated by gel chromatography.

In principle the same occurs in the cell in the in situ hybridization to detect certain genes or genome sections i.e. the specific incorporation of labelled nucleotides.

The above-mentioned primers i.e. short-chain oligonucleotides should form stable base pairs with the template strand as well as not be attacked by endogenous nucleases in order to ensure an optimal function.

This is fulfilled by oligonucleotides which contain the compounds according to the invention as building blocks instead of the classical nucleosides.

The same applies to longer chain polynucleotides and nucleic acids which contain such building blocks. These are also a subject matter of the present invention.

Corresponding oligonucleotides and their preparative precursors in the form of so-called phosphoramidites and H-phosphonates are therefore also a subject matter of the invention.

Oligonucleotides are nowadays usually produced by known methods in automated DNA/RNA synthesizers by solid phase synthesis.

Such methods of synthesis are based essentially on the stepwise reaction of the aforementioned phosphoramidites or H-phosphonates and hence the continuous linkage of these monomeric building blocks to form oligomers (see e.g. T. Brown & D. J. S. Brown in Oligonucleotides and Analogues-A Practical Approach, (1991) (Eckstein, F.,publ. IRL Press at Oxford University Press, Oxford, New York, Tokyo).

Figure 1:
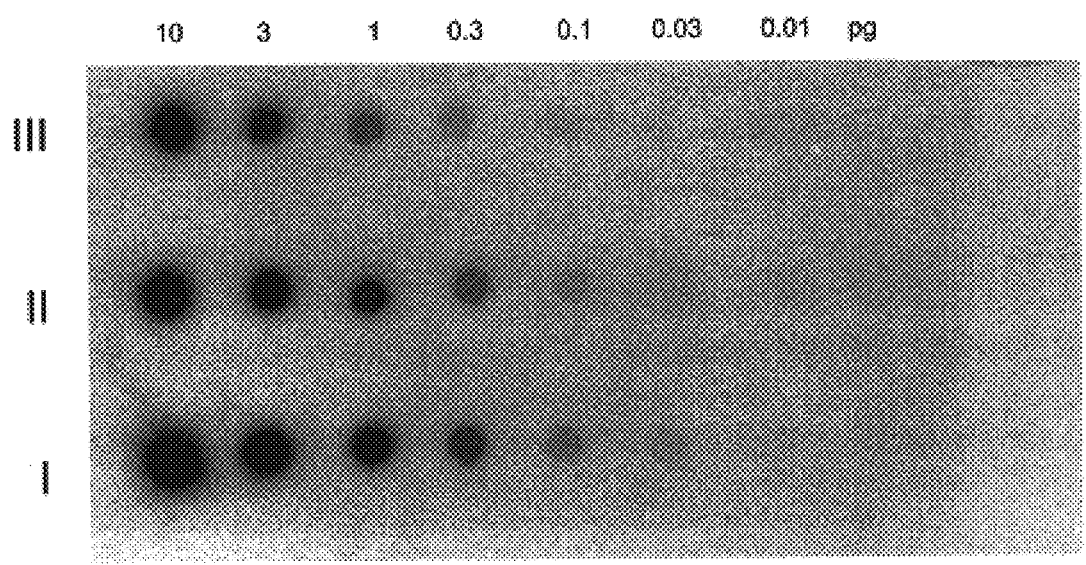
FIG. 1: I and II denote pBR 328-DNA labelled by DIG-dUTP incorporation (standard) and III denotes pBR 328-DNA labelled by the compound 3-(4-hydroxy-5-triphosphoryltetrahydrofuran-2-yl)-4-(digoxigeninyl-3-O-succinylaminocaproylamino-pentyl)-amino-pyrrol-2,5-dione synthesized according to example 6. They are applied to the gel at concentrations of 10 to 0.01 pg.

The invention is further elucidated by the following examples:

EXAMPLE 1

3-(4-Hydroxy-5-hydroxy-methyl-tetrahydrofuran-2-yl)-pyrrole-2,5-dione

The compound was prepared in a de novo synthesis according to Hosmane, R. S. et al. Bioorg. & Med.Chem. Lett. 3, 2847 (1993). Alternatively it can be obtained by Barton deoxygenation [Barton, D. H. R. & Motherwell, W. B. (1981) Pure Appl.Chem. 53, 15] from the 3,4-dihydroxy derivative (showdomycin) obtained by fermentation.

EXAMPLE 2

3-(4-Hydroxy-5-hydroxymethyl-tetrahydrofuran-2-yl)-4-bromo-pyrrole-2,5-dione 213 mg (1 mmol) 3-(4-hydroxy-5-hydroxymethyl-tetrahydrofuran-2-yl)-pyrrol-2,5-dione obtained according to example 1 is dissolved in 25 ml water saturated at RT with bromine and stirred for 3 hours at room temperature. Afterwards only a small amount of starting material is observed in the TLC. The solution is freed of excess bromine in a vacuum, adjusted to pH 7 and evaporated to an oil. It is taken up in a small amount of methanol and separated on a silica gel column with a mixture of chloroform/methanol 8:2. After evaporating the fractions, 140 mg (48%) of a pale yellow oil is obtained.

Elemental analysis: for $C_9H_{10}NO_5Br$ (MW292.2): $C_{calc}$36.9; $H_{calc}$3.4; $N_{calc}$4.8; $Br_{calc}$27.4; $C_{found}$37.35; $H_{found}$3.6; $N_{found}$4.5; $Br_{found}$27.8.

EXAMPLE 3

3-(4-Hydroxy-5-hydroxymethyl-tetrahydrofuran-2-yl)-4-(1,5-diaminopentyl)-pyrrole-2,5-dione 140 mg (ca. 0.5 mmol) of the bromine compound from example 2 is dissolved in 50 ml ethanol, admixed with 1.75 g (ca 10 mmol) diaminopentane dihydrochloride and heated to reflux for 5 hours. Afterwards the conversion is almost quantitative (compared to the lower spot of the bromine compound, ninhydrin positive) according to TLC (silica gel, chloroform/methanol 8:2). The reaction mixture is evaporated in a vacuum and used in example 4 without further purification.

EXAMPLE 4

3-(4-Hydroxy-5-hydroxymethyl-tetrahydrofuran-2-yl)-4-(N-trifluoroacetamidopentyl)-amino-pyrrole-2,5-dione The oily residue from example 3 (ca. 2 g) is dissolved in 50 ml anhydrous pyridine, undissolved material is removed by suction filtration and the filtrate is evaporated to dryness in a vacuum. It is taken up in 50 ml absolute pyridine and 0.75 ml (ca. 5 mmol) trifluoroacetic anhydride is added. After standing for 5 hours at RT the acylation is complete according to TLC. Subsequently the reaction solution is evaporated in a vacuum and coevaporated three times with methanol. It is taken in ca. 20 ml ethanol, filtered and chromatographed on silica gel with a mixture of chloroform/methanol (9:1). The combined fractions are evaporated, the residue is taken up in dioxane and lyophilized. 110 mg (53% of theory) of the desired compound is obtained.

Elemental analysis for $C_{16}H_{23}N_3O_6F_3$ (MW 410.4): $C_{calc}$46.8; $H_{calc}$5.6; $N_{calc}$10.2; $F_{calc}$13.9; $C_{found}$47.35; $H_{found}$5.9; $N_{found}$10.5; $F_{found}$13.8.

EXAMPLE 5

3-(4-Hydroxy-5-triphosphoryl-tetrahydrofuran-2-yl)-4-(N-trifluoroacetamidopentyl)-amino-pyrrole-2,5-dione 40 mg (0.1 mmol) of the protected nucleoside from example 4 is converted by phosphorylation with $POCl_3$ into the 5'-monophosphate according to the method of Yoshikawa et al. [Tetrahedron Lett. 50, 5065 (1967)]; the desired triphosphate is obtained from this in a yield of 30 mg (46%) according to the method of Hoard & Ott [J.Am.Chem.Soc. 87, (1965)] after activation with carbonyldiimidazole and reaction with pyrophosphoric acid and subsequent ion exchange chromatography on DEAE Sephadex.

$^{31}$P-NMR (0.1 M EDTA/D$_2$O/Eth$_3$N): −5.2(d,P-γ); −10.3 (d,P-α); −21.0 (t,P-β).

EXAMPLE 6

3-(4-Hydroxy-5-triphosphoryl-tetrahydrofuran-2-yl)-4-(N-fluoresceinyl-carboxamido-pentyl)-amino-pyrrole-2,5-dione 25 mg (0.038 mmol) of the trifluoroacetyl-protected compound from example 5 is allowed to stand for 1 h at RT in 5 ml concentrated ammonia solution and subsequently evaporated in a vacuum. The residue is taken up in 5 ml 0.1 M borate buffer, pH 8.5 and admixed with a solution of 25 mg (0.05 mmol) 5(6)-carboxyfluorescein-N-hydroxy-succinimide ester in 5 ml amine-free dimethyl formamide. It is allowed to stand overnight at room temperature. The reaction mixture is applied to a DEAE Sephadex column (30×1 cm) and eluted with a linear LiCl gradient (200 ml H$_2$O to 0.4 M LiCl). After combining the appropriate fractions, evaporating, precipitating the concentrate in acetone/ ethanol (2:1) and drying, 25 mg (ca. 50%) of the title substance is obtained.

Spectral data. (0.1 M phosphate buffer, pH 9.0:

excitation$_{max}$ [nm]: 495;

emission$_{max}$: [nm]: 521

The 3-(4-hydroxy-5-triphosphoryl-tetrahydrofuran-2-yl)-4-(digoxigeninyl-3-O-succinyl-aminocaproylamino-pentyl)-amino-pyrrole-2,5-dione was prepared in a corresponding manner by reacting the compound from example 5 with digoxigenin-3-O-succinyl-aminocaproic acid-N-hydroxy-succinimide ester.

EXAMPLE 7

3-(4-Hydroxy-5-hydroxymethyl-tetrahydrofuran-2-yl)-1,3-oxazine-2,6-dione

The compound was obtained by Barton deoxygenation [Barton, D. H. R. & Motherwell, W. B. (1981) Pure Appl.Chem. 53, 15] from the 3,4-dihydroxy derivative (oxazinomycin) obtained by fermentation.

EXAMPLE 8

3-(4-Hydroxy-5-hydroxymethyl-tetrahydrofuran-2-yl)-4-bromo-1,3-oxazine-2,6-dione The derivative was obtained by brominating the starting compound from example 7 as described in example 2.

EXAMPLE 9

3-(4-Hydroxy-5-hydroxymethyl-tetrahydrofuran-2-yl)-4-(1,5-diaminopentyl)-1,3-oxazine-2,6-dione 150 mg (0.5 mmol) of the bromine compound from example 8 was converted into the title compound according to the method of example 3. This was finally reacted with fluorescein-labelled triphosphate without further purification according to the methods of examples 4, 5 and 6.

EXAMPLE 10

3-(4-Hydoxy-5-hydroxymethyl-tetrahydrofuran-2-yl)-2,6-diamino-5-chloro-pyrazine

The derivative was synthesized according to Townsend, L. B. et al. Tetrahedron Lett. 36, 8363 (1995).

EXAMPLE 11

3-(4-hydroxy-5-hydroxymethyl-tetrahydrofuran-2-yl)-2,6-diamino-5-chloro-pyrazine 264 mg (1 mmol) 3-(4-Hydroxy-5-hydroxymethyl-tetrahydrofuran-2-yl)-2,6-dihydroxy-5-chloro-pyrazine from example 10 was subjected to a deamination reaction in a mixture of 50 ml 80% acetic acid and 700 mg (10 mmol) NaNO$_2$. After standing for 5 hours at RT, the reaction was almost complete according to TLC. 2 g urea was added to the reaction mixture to destroy excess nitrite and stirred for a further three hours at RT. Afterwards the solution was applied to an activated carbon column (Carboraffin C, ca. 50 ml volume), adequately washed and the desired product was eluted with ethanol/water/ammonium. 230 mg (ca. 87%) of a viscous oil resulted after evaporation which was used in the next stage without further purification.

EXAMPLE 12

3-(4-Hydroxy-5-hydroxy-methyl-tetrahydrofuran-2-yl)-2,6-dihydroxy-5-(1,8-diamino-3,6-dioxa-octyl)-pyrazine 200 mg (0.75 mmol) of the oil from example 11 was dissolved in 30 ml ethanol, 555 mg (3.75 mmol) 1,8-diamino-3,6-dioxa-octane was added and it was heated for 3 hours to ca. 60° C. Subsequently the solvent and amine were removed in an oil pump vacuum and the residue was further reacted without further purification by reaction with trifluoroacetic anhydride in pyridine as described in example 4.

EXAMPLE 13

3-(4-Hydroxy-5-triphosphoryl-tetrahydrofuran-2-yl)-2,6-dihydroxy-5-[N-trifluoro-acetamido-(3,6-dioxa)-octyl]-amino-pyrazine 150 mg of the trifluoracetylated derivative from example 12 was converted into the title compound according to Yoshikawa and Hoard & Ott as described in example 5. The desired tripliosphate was obtained in a yield of 120 mg (40%) after ion exchange chromatography on DEAE Sephadex.

$^{31}$P-NMR (0.1 M EDTA/D$_2$O/Eth$_3$N): −5.1(d,P-γ); −10.6 (d,P-α); −20.8 (t,P-β).

EXAMPLE 14

3-(4-Hydroxy-5-triphosphoryl-tetrahydrofuran-2-yl)-2,6-dihydroxy-5-[N-tetramethyl-rhodaminyl-5,6-carboxamido-(3,6-dioxa)-octyl]-amino-pyrazine 20 mg of the triphosphate from example 13 were reacted—after cleavage of the trifluoroacetyl protective group with ammonia solution (as described in example 6)—with 20 mg tetramethylrhodamine-5(6)-carboxylic acid-N-hydroxy-succinimide ester in 0.1 M sodium borate buffer, pH 8.5/DMF as described in example 6 and purified. 12 mg of the TMR-labelled product was obtained. Spectral data (0.1 M Na-borate buffer, pH 8.5):

excitation $_{max}$ [nm]: 551;
emission$_{max}$: [nm]: 575

EXAMPLE 15

Non-radioactive DNA labelling and detection by incorporation of 3-(4-hydroxy-5-triphosphoryltetrahydrofuran-2-yl)-4-(digoxigeninyl-3-O-succinylaminocaproylamino-pentyl)-amino-pyrrole-2,5-dione The DNA labelling and the DNA detection were carried out using the commercially available kit from the Boehringer Mannheim Company (order No. 1093 657). All essential process steps are described in the working instructions.

For the labelling reaction the DIG-dUTP in the dNTP mixture in the kit was substituted by a 3-(4-hydroxy-5-triphosphoryl-tetrahydrofuran-2-yl)-4-(digoxigeninyl-3-O-succinyl-aminocaproylamino-pentyl)-amino-pyrrole-2,5-dione (synthesized as described in example 6).

The immunological detection reaction showed that incorporation of the inventive compound of example 6 resulted in a detection sensitivity of the labelled DNA which is similar to the use of DIG-dUTP.

The result which demonstrates the detection and the achieved sensitivity of the system is shown in FIG. 1.

What is claimed is:

1. A compound of the general formula

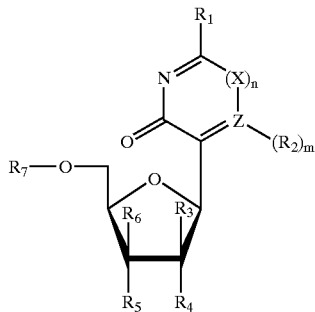

in which
$R_1$ and $R_2$ can be the same or different and represent hydrogen, oxygen, halogen, hydroxy, thio or substituted thio, amino or substituted amino, carboxy, lower alkyl, lower alkenyl, lower alkinyl, aryl, lower alkyloxy, aryloxy, aralkyl, aralkyloxy or a reporter group, $R_3$ and $R_4$ each represent hydrogen, hydroxy, thio or substituted thio, amino or substituted amino, lower alkyloxy, lower alkenoxy, lower alkinoxy, a protecting group or a reporter group, $R_5$ represents hydrogen, hydroxy, thio or substituted thio, amino or a substituted amino group, a reactive trivalent or pentavalent phosphorus group such as e.g. a phosphoramidite or H-phosphonate group, an ester or amide residue that can be cleaved in a suitable manner or a reporter group, $R_4$ and $R_5$ together form a further bond between C-2' and C-3' or an acetal group, $R_6$ represents hydrogen or a hydroxy, thio or substituted thio, amino or substituted amino group, $R_7$ represents hydrogen, a monophosphate, diphosphate or triphosphate group or the alpha, beta or gamma thiophosphate analogue of this phosphoric acid ester or a protective group as well as possible tautomers and salts thereof, X denotes methylene or methine substituted with halogen, hydroxy, thio or substituted thio, amino or substituted amino, carboxy, lower alkyl, lower alkenyl, lower alkinyl, aryl, lower alkyloxy, aryloxy, aralkyl, aralkyloxy or a reporter group, or oxygen and n=0 or 1, Z denotes nitrogen or carbon provided that if Z denotes nitrogen, m is zero (0) and if X represents methylene, substituted methylene or substituted methine, Z cannot be carbon and if X denotes oxygen, Z cannot be nitrogen and if Z denotes carbon, $R_2$ cannot be hydrogen.

2. The compound as claimed in claim 1, in which $R_1$ can represent oxygen, $R_2$ can represent hydrogen or a reporter group, $R_3$ and $R_4$ can represent hydrogen, $R_5$ can represent hydroxy, hydrogen, a reactive trivalent or pentavalent phosphorus group, $R_6$ can represent hydrogen and $R_7$ can represent hydrogen, mono-, di-, or triphosphate groups.

3. An oligonucleotide comprising a compound of claim 2.

4. The compound as claimed in claim 1 wherein $R_1$ represents hydrogen, hydroxy, an amino group, a substituted amino group or a reporter group, $R_2$ represents an amino or substituted amino group or a reporter group, $R_3$ represents hydrogen, $R_4$ represents hydrogen, hydroxy, amino or substituted amino, lower alkyloxy, lower alkenoxy, lower alkinoxy, $R_5$ represents hydrogen, hydroxy, thio, an amino or substituted amino group, a phosphoramidite or a reporter group, $R_4$ and $R_5$ together represent an acetal group, $R_6$ represents hydrogen and $R_7$ represents a triphosphate group.

5. An oligonucleotide comprising a compound of claim 4.

6. The compound as claimed in claim 1 in which X denotes oxygen and at the same time Z represents carbon substituted with $R_2$ or Z denotes nitrogen and at the same time X represents methylene or methine substituted with amino or substituted amino, with carboxy or with a reporter group.

7. An oligonucleotide comprising a compound of claim 6.

8. The compound as claimed in claim 1 in which X=0 and Z represents methine substituted with amino or substituted amino, with carboxy or with a reporter group are a further preferred embodiment.

9. An oligonucleotide comprising a compound of claim 8.

10. The compound as claimed in claim 1, wherein the acetal group of the residues $R_4$ and $R_5$ is substituted with a reporter group.

11. An oligonucleotide comprising a compound of claim 10.

12. The compound as claimed in claim 1, wherein the reporter group denotes a hapten, a fluorophore, a metal-chelating group, a luminophore, a protein or an intercalator.

13. An oligonucleotide comprising a compound of claim 12.

14. The compound as claimed in claim 1, in which the reporter group is linked via a linker group.

15. An oligonucleotide comprising a compound of claim 14.

16. A method for synthesizing a nucleic acid comprising incorporating the compound of claim 1 into the nucleic acid by a DNA or RNA polymerase.

17. A method for synthesizing an oligonucleotide comprising incorporating the compound of claim 1 into the oligonucleotide wherein $R_7$ is a phosphoramidite or H-phosphonate.

18. An oligonucleotide comprising a compound of claim 1.

19. A nucleic acid comprising a compound of claim 1.

* * * * *